United States Patent
Conte et al.

(10) Patent No.: US 9,057,047 B2
(45) Date of Patent: Jun. 16, 2015

(54) DEVICE FOR CELL CULTURE

(75) Inventors: Pierfranco Conte, Pisa (IT); Massimo Dominici, Ferrara (IT); Gianni Bellini, Medolla (IT); Matteo Brogli, Ferrara (IT)

(73) Assignee: RIGENERAND SRL, Medolla (Modena) (IT)

( * ) Notice: Subject to any disclaimer, the term of this patent is extended or adjusted under 35 U.S.C. 154(b) by 709 days.

(21) Appl. No.: 13/056,111

(22) PCT Filed: Aug. 6, 2009

(86) PCT No.: PCT/IB2009/053424
§ 371 (c)(1),
(2), (4) Date: Feb. 4, 2011

(87) PCT Pub. No.: WO2010/016023
PCT Pub. Date: Feb. 11, 2010

(65) Prior Publication Data
US 2011/0129913 A1 Jun. 2, 2011

(30) Foreign Application Priority Data
Aug. 6, 2008 (IT) .............................. MO2008A0215

(51) Int. Cl.
C12M 1/12 (2006.01)
C12M 1/04 (2006.01)
C12M 1/00 (2006.01)

(52) U.S. Cl.
CPC ............... *C12M 23/24* (2013.01); *C12M 23/00* (2013.01); *C12M 23/14* (2013.01); *C12M 29/10* (2013.01)

(58) Field of Classification Search
CPC ...... C12M 23/00; C12M 23/14; C12M 23/24; C12M 29/10
USPC ........... 435/284.1, 289.1, 293.1, 297.5, 299.1
See application file for complete search history.

(56) References Cited

U.S. PATENT DOCUMENTS

| 5,545,223 | A | 8/1996 | Neuenfeldt |
| 5,843,766 | A | 12/1998 | Applegate |
| 5,395,847 | A | 8/1999 | Smith |
| 5,935,847 | A * | 8/1999 | Smith et al. ................. 435/297.5 |
| 6,773,425 | B1 * | 8/2004 | Tamari .......................... 604/403 |
| 6,900,055 | B1 * | 5/2005 | Fuller et al. .................... 435/395 |
| 2005/0054087 | A1* | 3/2005 | Cote et al. .................. 435/299.1 |
| 2007/0122894 | A1 | 5/2007 | Richardson Casella |

\* cited by examiner

*Primary Examiner* — Michael Hobbs
(74) *Attorney, Agent, or Firm* — Themis Law (57) ABSTRACT

A device for cell culture includes a container body, which has an internal compartment to contain a quantity of cells to be cultured and a culture surface for the cells placed in the internal compartment; an introduction opening for introducing the cells to be cultured in the internal compartment; the container body having a first half shell and a second half shell, which can be fixed in mutually facing relation by a removable fixing system and which together define the internal compartment and the culture surface; and at least one out feed opening for a transport and/or culture fluid for the cells.

12 Claims, 6 Drawing Sheets

DEVICE FOR CELL CULTURE

FIELD OF THE INVENTION

The invention relates to a device for cell culture.

BACKGROUND ART

Cells have been long known to be cultured in containers specially designed for cell culture.

In prior art, a predetermined number of cells to be cultured is suspended in liquid solutions, which are later introduced into special containers in which cell proliferation occurs, in particular environmental conditions prepared for is this purpose, with cells possibly adhering to a special support.

The environmental conditions for culture may require cells to be supplied with oxygen and heated to a predetermined temperature.

For this reason, the cells to be cultured are introduced into containers that are later placed into an incubator whose environment is maintained in sterile conditions and with controlled temperature and gas composition.

Cell culture may essentially be carried out with two types of methods, i.e. a static method and a dynamic method.

In short, according to the static method, a cell-containing solution is placed in a culture container and is left lying therein with a second culture solution until cells proliferate to predetermined amounts, whereas, according to the dynamic method a solution that contains cells to be cultured is introduced into the culture container in which a second culture solution is later circulated between an inlet and an outlet thereof, and in which appropriate support structures hold the cells in the container while causing the per fused culture solution to flow out.

This solution may be re-circulated by a special circuit of pipes or is designed to be lost.

The support structures are used when the solution flows require cell binding elements, i.e. elements whose morphological structure or physic—chemical features promote cell binding.

When the cell culture provides the required amounts of cells, both on the surfaces of containers and on those of the binding elements, cells are recovered using a chemical or biological agent which is later removed by washing and by a mechanical scraping action in combination with washing.

The above described prior art suffers from certain drawbacks.

A first drawback is that the cell culture is exposed to pollution by environmental agents during handling, because containers are often open or designed to be closed by plugs, but have no device for preserving sterility where cell culture occurs.

Another drawback is that, before transporting or administering the cultured cells to a patient, these are required to be transferred into a suitable container, which should affect as little as possible their function until administration or use.

However, the sterile chain is broken during such transfer, as the containers in which the cells are transported are opened several times.

A further drawback is that the prior art containers are alternately constructed and designed for either static or dynamic culture and cannot be used for both.

Another drawback is that the prior art containers cannot easily exchange gases, particularly oxygen, with the cells, especially when these are placed in areas of the containers that are far from oxygen inlet points.

A further drawback is that, when using cell binding elements, these must be held fully immersed in the solution in which the cells are suspended, but without allowing the level of such solution to be too high above such elements, because the solution acts as a barrier for the passage of oxygen (or other gases) to the cells, and the higher the level in the container, the harder is gas exchange with the cells.

It shall be noted in this respect that, during their life cycle, cells generally is absorb oxygen and emit carbon dioxide to be evacuated from the containers to prevent saturation.

A further drawback of dynamic culture is that continuous passage of solution flows may generate turbulence in the container, and thus hinder cell proliferation.

Yet another drawback is that the step of detachment of cultured cells from their culture surfaces causes damages to part of the detached cells, and reduces culture effectiveness.

A further drawback is that limited culture spaces are available in prior art devices.

Another drawback is that a considerable part of the internal volume of culture devices has to be left empty for free gas circulation.

Another drawback is that some culture containers require special treatments of culture surfaces to promote bonding of the cells to be cultured.

OBJECTS OF THE INVENTION

It is an object of the invention to improve the prior art.

Another object of the invention is to provide a cell culture device that maintains a sterile culture field from the beginning to the end of the culture cycle.

Another object of the invention is to allow homogeneous gas exchange between the cells and the culture medium throughout the culture device, whenever this is required by the type of cells to be cultured, thereby obtaining a large number of available cells in a very short culture time.

A further object of the invention is to allow administration of the cultured cells to a patient without affecting the sterility of the culture zone and without requiring any transfer or transportation of cells in auxiliary containers.

Another object of the invention is to allow either static or dynamic culture of cells in one container, that can be used for both.

A further object of the invention is to provide a cell culture device that can be used with known culture and administration protocols, without requiring any particular change or using specially constructed devices.

Yet another object of the invention is to considerably limit turbulence and facilitate air exhaust in case of dynamic culture.

A further object of the invention is to provide a cell culture device that can be easily and directly applied to a patient.

A further object of the invention is to provide a cell culture device that ensures excellent culture efficiency, i.e. a large number of cells with respect to the size of the surface covered by the culture device and limits volume requirements of culture means.

A further object of the invention is to provide a cell culture device that doesn't require the use of traditional incubator apparatus.

According to one aspect of the invention, it is provided a device for cell culture, comprising: a container body which has an internal compartment to contain a quantity of cells to be cultured and a culture surface for said cells placed in said internal compartment; an introduction opening for introducing said cells to be cultured in said compartment; characterized in that said container body comprises: first half shell means and second half shell means is which can be fixed in mutually facing relation by removable fixing means and which together define said internal compartment and said culture surface; at least one outfeed opening for a transport and/or culture fluid for said cells.

The device for cell culture, e.g. for the culture of stem cells, allows:
- culture to be carried out in perfectly aseptic conditions, i.e. avoiding external contaminations;
- quick and convenient provision of cells ready for use, such as for administration to patients;
- transportation of the device during cell culture without using auxiliary apparatus for preservation and transport thereof;
- provision of a large culture surface with respect to the size of the device;
- substantially homogeneous oxygenation of all cultured cells and in all culture areas of the device;
- use in combination with known culture, transfusion and perfusion apparatus;
- aseptic removal of the cell culture support from the culture device;
- prevention of turbulence in case of dynamic cultures.

BRIEF DESCRIPTION OF THE DRAWINGS

Further features and advantages of the invention will be more readily apparent upon reading of the detailed description of a preferred non exclusive embodiment of a device for cell culture, which is shown as a non limiting example by the annexed drawings, in which.

EMBODIMENTS OF THE INVENTION

Figures 1, 2, 2A:
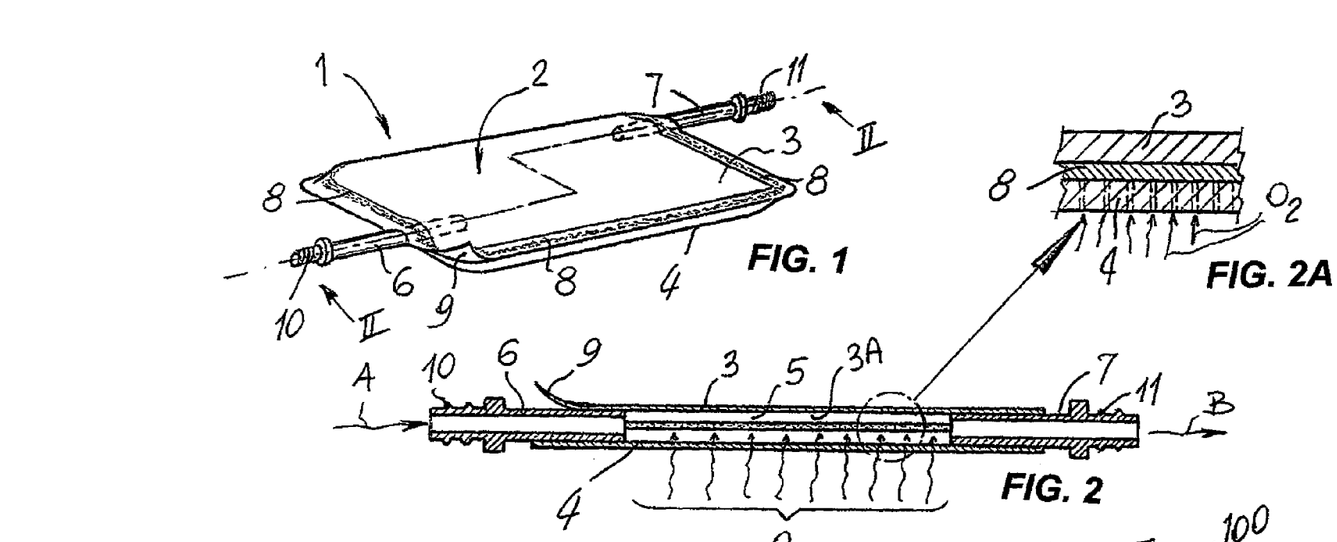
FIG. 1 is a perspective and schematic view of a first embodiment of a device for cell culture of the invention.
FIG. 2 is a longitudinal sectional view of the device of FIG. 1, as taken along two offset planes II-II.
FIG. 2A is a cross sectional view of a detail of a peripheral area of the device of FIG. 2.

Referring to FIGS. 1 and 2, numeral 1 designates a first embodiment of a device for cell culture.

According to this embodiment, the device 1 comprises a container body 2 which is obtained by joining two half-shells 3 and 4, formed of respective sheet elements in mutual facing relation.

At least one of these two half-shells 3 and 4, such as the one designated, in FIG. 1, by numeral 4, is made from a gas-porous material, such as a membrane.

However, both half-shells 3 and 4 are made of hydrophobic materials, which make them liquid-impervious.

An internal compartment 5 is defined between the two half-shells 3 and 4, and is designed to receive the cells to be cultured, which are contained in a liquid transport solution that flows through the device 1 in the direction of arrows "A" and "B", from an inlet line segment, designated by numeral 6 to an outlet line section, designated by numeral 7.

It shall be noted that, in this embodiment, the two line segments 6 and 7, i.e. the inlet and outlet sections respectively (although they may be exchanged), are placed at opposite sides of the container body 2, to accomplish a function to be described in greater detail below.

As shown in FIGS. 1 and 2, the two half-shells 3 and 4 are joined together along their respective peripheral edges by a peelable adhesive bead 8, allowing the two half-shells 3 and 4 to be separated without being damaged.

In order to facilitate such separation, at least one of the two half-shells, namely the half-shell 3, is equipped with a tab 9 that, in spite of adhesion, is separate from the opposite half-shell 4 and may be easily grasped and pulled for progressive mutual separation of the two half-shells 3 and 4.

The two line segments 6 and 7 may have connectors 10 and 11 at their outward ends, which have standard characteristics (such as connectors known as "luer"), for connection to corresponding ends of pipes of a medical circuit, such as an infusion circuit or a syringe.

In this embodiment of the device 1 for cell culture, the half-shell 3 defines an inner face 3A that forms a culture surface, with the cells being designed to adhere thereto during culture.

Figure 3:
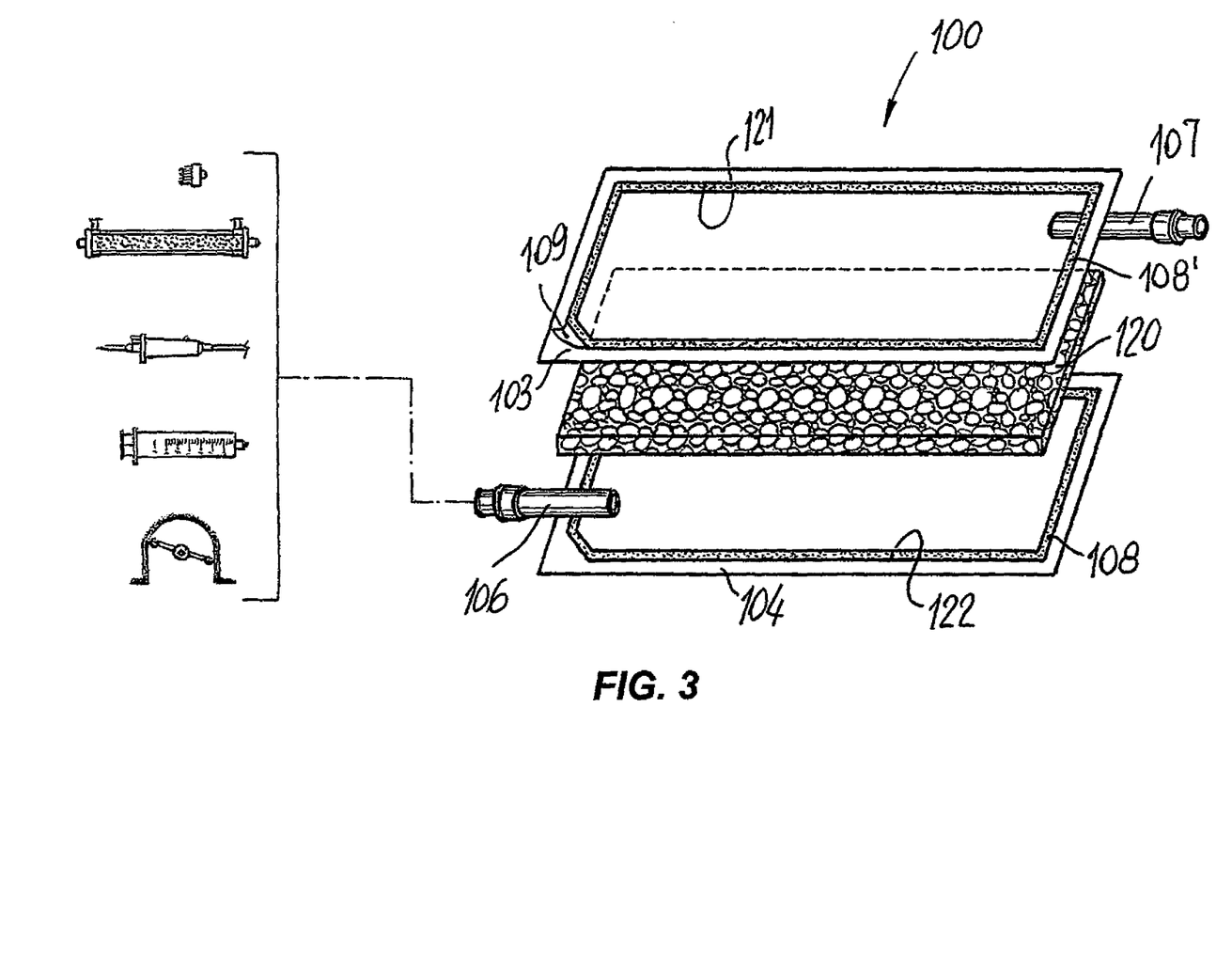
FIG. 3 is a perspective and exploded view of a possible alternative embodiment of a device for cell culture of the invention.
Figure 4:
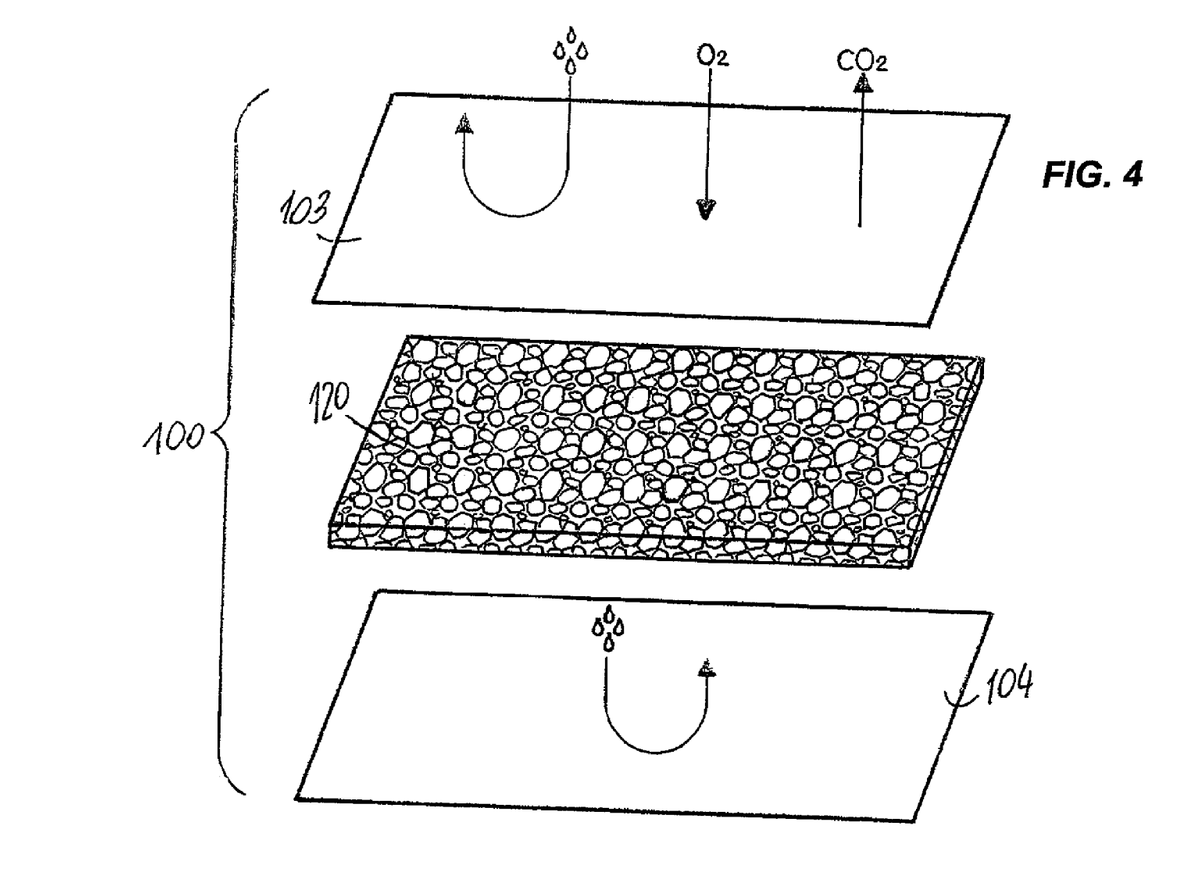
FIG. 4 is a schematic perspective and exploded view of the device of FIG. 4, on a slightly larger scale.
Figure 5:
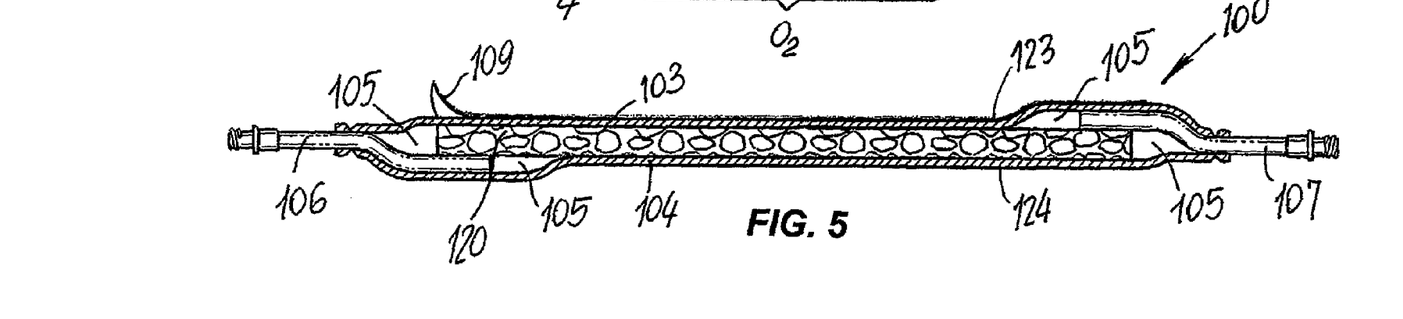
FIG. 5 is a longitudinal cross sectional view of the device of FIG. 3.

Referring to FIGS. 3, 4, 5, there is shown a second embodiment of a device for cell culture designated by numeral 100.

Once again, the device 100 comprises a container body 102 which is is obtained by adhesively joining two rigid or semi-rigid half-shells 103, 104 in mutual facing relation, to define an internal compartment 105 therebetween.

Like in the previous embodiment, the two half-shells 103 and 104 are adhered to each other in an un-removable fashion or using a peelable adhesive bead 108, which is provided at the periphery of the internal compartment 105.

The latter is designed to receive a culture element 120 of substantially flat shape, which has a substantially porous or rough culture surface, to promote adhesion of the cells to be cultured.

The two half-shells 103 and 104 have surface openings 121 and 122 allowing access to the internal compartment 105 and to the culture element 120.

The two surface openings 121 and 122 can be sealed by sheet elements 123 and 124 that adhere to the respective half-shells 103 and 104 by corresponding peelable adhesive beads 108.

At least one of these sheet elements 123 and 124 is formed of a gas-porous material, namely porous to oxygen and carbon dioxide, which is also hydrophobic to prevent passing through of liquid flows.

The pores of such hydrophobic material indicatively have a size from 0.005 micron to 0.45 micron.

At least one of these sheet elements, e.g. the sheet element 123, has a tab 109 that does not adhere to the corresponding half-shell 103 and is designed to be grasped by a user to open the internal compartment 105, by removing the sheet element 123 from the corresponding half-shell 103.

This embodiment also has two line segments 106 and 107 that act as an inlet and an outlet respectively (possibly exchangeable).

The line segment 106 is designed to receive the cells to be cultured, which are suspended in a liquid transport solution, whereas the line segment 107 is designed to be used for the outflow of the liquid solution once the cells to be cultured are released onto the culture element 120.

It shall be noted that the culture element 120 is held in contact with both half-shells 103, 104, which facilitates exchange of oxygen and removal of carbon dioxide through the pores of the sheet elements 123, 124 if both are gas-permeable.

Figure 7:
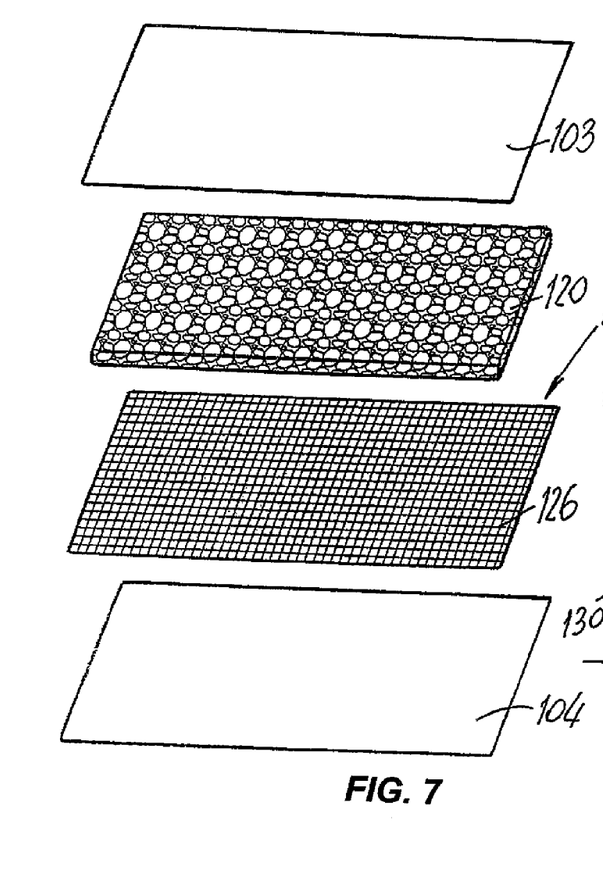
FIG. 7 is a perspective exploded view of a first embodiment of a device of the invention having a support element.
Figure 8:
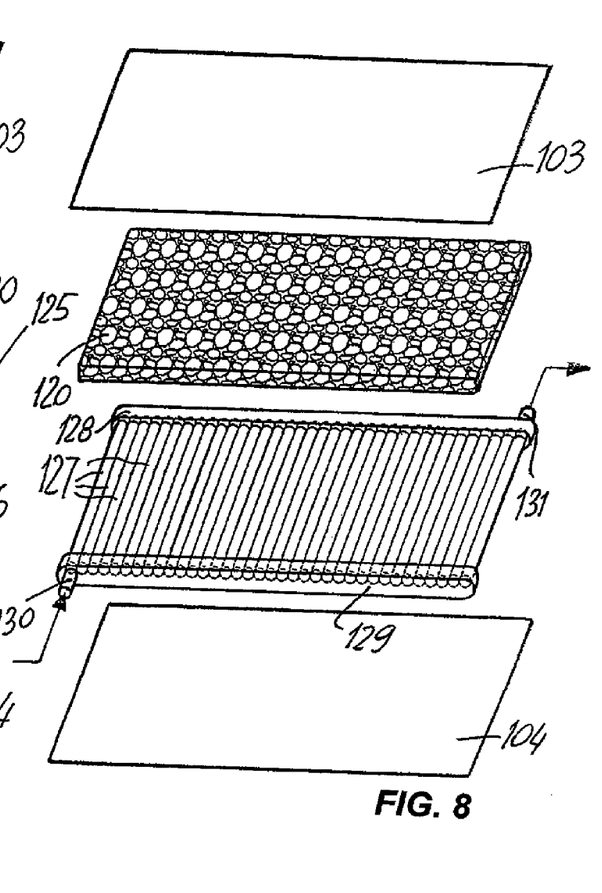
FIG. 8 is a perspective exploded view of a second embodiment of a device of the invention having a support element.
Figure 10:
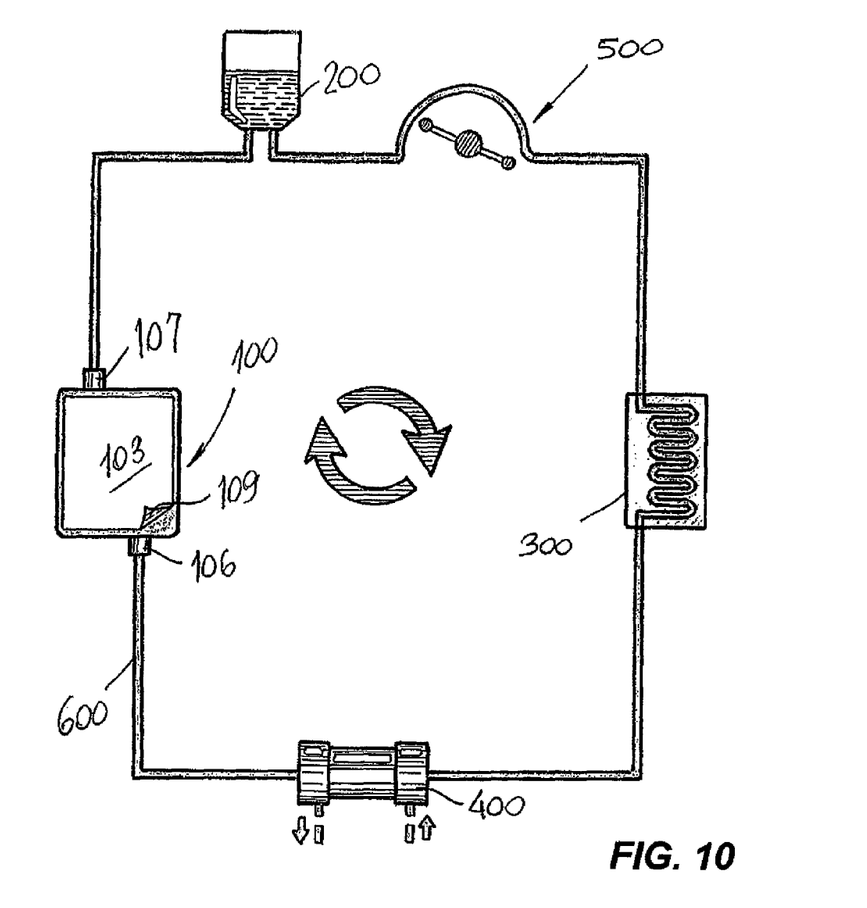
FIG. 10 is a schematic view of a cell culture circuit which incorporates a device for cell culture of the invention.

Referring to FIGS. 7, 8, 10, it shall be noted that a substantially flat support element 125, which is designed to support the culture element 120, is interposed between the culture element 120 and one of the half-shells, e.g. the half-shell 104.

In a first embodiment, as shown in FIG. 7, this support element 125 comprises a grid-like body 126 composed of a matrix of perpendicular wires.

In a second embodiment, as shown in FIG. 8, this support element 125 comprises a weft of capillary segments 127 with homologous ends coming into a warp comprising two connecting elements 128 and 129.

Each of these connecting elements 128 and 129 has an inlet or outlet port, designated by 130 and 131 respectively, which may receive an auxiliary liquid that is designed to flow into the two connecting elements 128 and 129 and into the capillary segments 127, such as a heated auxiliary liquid.

Both the grid-like body 126 and the weft of capillary segments 127 and the connecting elements 128 and 129 may be placed outside one of the sheet elements 123 or 124, which in this case is not made of a porous material.

The device for cell culture has the following operation.

In the first embodiment, a liquid solution with the cells to be cultured suspended therein, is caused to enter the internal compartment 5 of the container body 2, once the line segment 6 has been previously connected to a source that delivers such solution filled with cells, such as stem cells, and the line segment 7 is held open to discharge the air contained in the empty device.

When the cells are in the internal compartment 5 they tend to adhere to the culture surface 3A that coincides with the inner face of the half-shell 3.

The other half-shell 4 is made of a porous material, such as silicone, polypropylene (PP), polymethyl pentene (PMP) or a combination of layers of polymeric materials or gas-permeable polyolefins, to allow effective gas exchange between the outside and the internal compartment 5, i.e. to allow the ingress of the oxygen required for cell survival, while preventing the passage, and hence the loss of the liquid solution, thereby keeping the internal compartment 5 aseptic.

At the same time, the carbon dioxide produced by the cells during the culture cycle is eliminated through the pores of the half-shell 4.

The liquid solution, free of the cells or most of them, is discharged at predetermined times through the line segment 7 and replaced with a cell culture liquid or possibly re-circulated by a suitable recirculation circuit, which is known to the skilled person and will not be described herein in detail.

Once culture in the internal compartment 5 has provided the desired amount of cells, the device 1 is ready for application to a patient or for collection of the cells being produced.

When the device 1 is to be transported, and in static culture conditions, plugs are fitted to the corresponding connectors 10 and 11 to isolate the device from the outside and conveniently transport it without requiring any additional auxiliary transport apparatus, while keeping the cell culture contained therein aseptic.

When the device 1 reaches, for instance, a patient for administering the cells to an area affected by a disease that requires local administration of cells, an operator pulls the tab 9 to separate the half-shell 3 from the half-shell 4, and thus make the culture surface 3A accessible for direct application to the area affected by the disease, by laying it in contact therewith.

In the other embodiment of the culture device 100, cell seeding in the compartment 105 occurs as described above, but the cells deposit on the three-dimensional surface of the culture element 120 while the liquid solution passes therethrough from the inlet line segment 106 to the outlet line segment 107.

As most of the solution is forced to pass through the culture element 120, the cells are allowed to adhere thereto and a substantially laminar flow of the solution is maintained, with no vortex or turbulence being generated.

Also in this case, once the ends of the line segments 106 and 107 have been closed by special plugs and a desired amount of cells has been reached after a predetermined time, the device 100 is ready for application to a patient or for collection of the cells being produced.

Once again, the device 100 allows cell culture and is capable of being carried to the patient while ensuring that the internal compartment 105, and hence the cell culture environment, is kept aseptic, without using any additional transport members and any hypothermal or hypoxic treatments, that are potentially noxious for the cells.

Figure 6A:
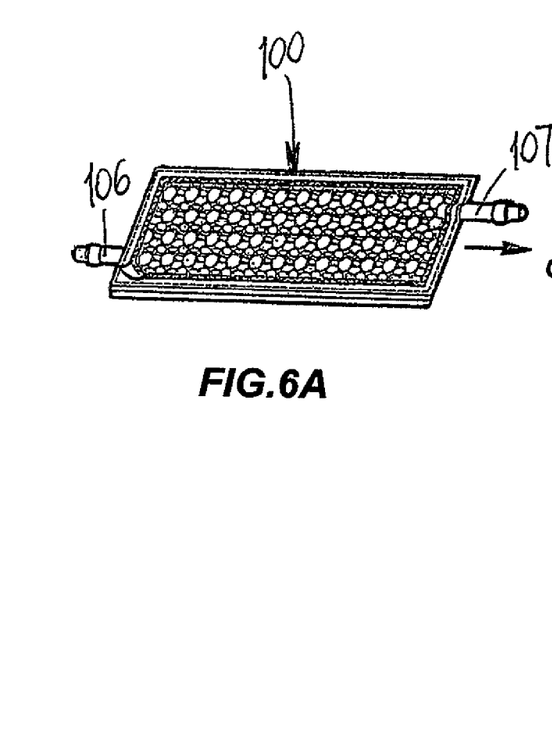
FIGS. 6A, 6B, 6C are perspective views of three steps of the process for opening the device of FIG. 3, to recover an internal culture element to be administered to a patient.
Figure 6B:
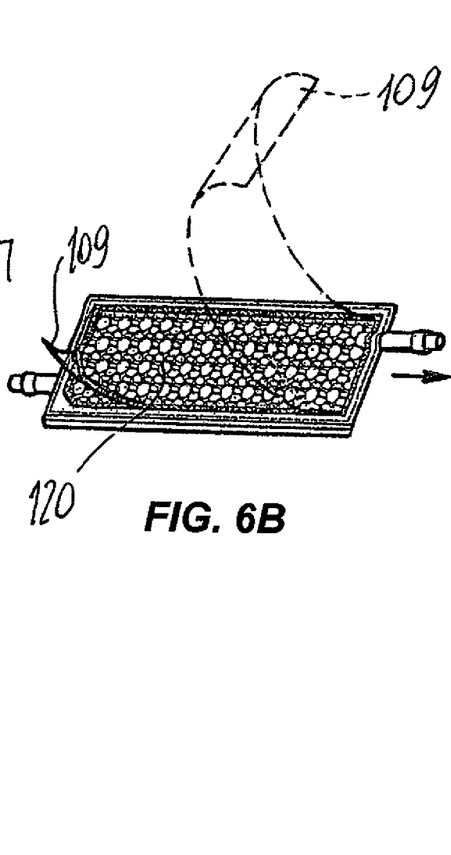
Figure 6C:
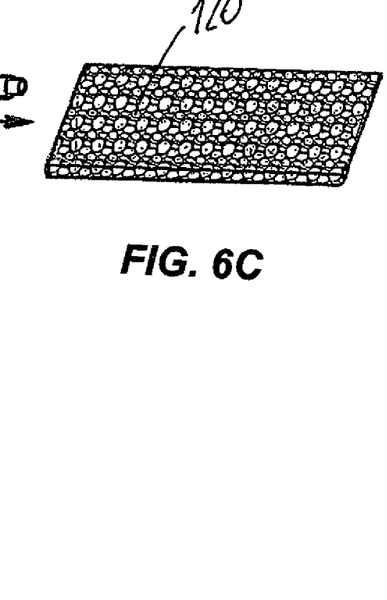

For application, the user shall simply pull the tab 109 to peel the whole sheet element 123 off the half-shell 103 and access the internal compartment 105 and the culture element 120 through the surface opening 121.

Then, the user picks up the culture element 120 and puts it in direct contact with the diseased area.

It shall be noted that the culture element 120 may be also formed of degradable materials that are designed to crumble with time and to automatically release the cells without requiring a separation step with the use of chemicals and/or mechanical scraping, that might damage a considerable number of them.

Furthermore, for certain applications a bio-absorbable material may be used for the culture element 120.

In certain cases, the device 100 may have the grid-like support element 126 for supporting the culture element 120 interposed between one of the half-shells 103 or 104 and the culture element 120 (or disposed external to both).

Figure 9:
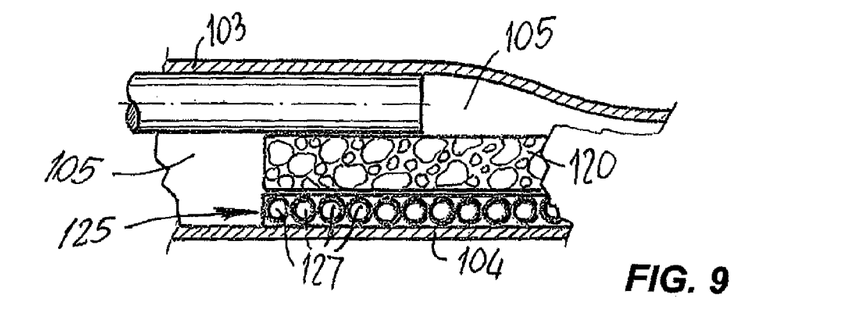
FIG. 9 is an interrupted longitudinal cross sectional view of the device for cell culture of FIG. 8.

Furthermore, when the cell culture environment needs to be heated without using any traditional incubation method, the support element 125 is designed in the form of a set of capillary segments 127 in parallel side-by-side relation, and connected at their homologous ends by two respective connecting elements 128 and 129.

Therefore, an auxiliary heated liquid may be circulated within the capillaries 127 and both connecting elements 128 and 129, by introducing it through the inlet port 130 and discharging it through the outlet port 131.

In a different embodiment, a device for cell culture according to the invention includes a size increase system to increase the size of the culture surface. The size increase system may include a series of bends obtained in the culture surface and in relief in the internal compartment.

Referring to FIG. 10, it may be appreciated that the device 1 or 100 for cell culture may be also easily introduced in a conventional circuit known for this purpose, which comprises a tank 200, a heater 300, an oxygenator 400 and a pump 500, disposed in series along a solution transport line designated by numeral 600, which is connected to the connectors 10 and 11, or 106 and 107 of the device for cell culture 1 or 100 respectively.

What is claimed is:

1. A device for cell culture, comprising:
    a container body which has an internal compartment to contain a quantity of cells to be cultured and a culture surface for said cells placed in said internal compartment; and
    an introduction opening for introducing said cells to be cultured in said compartment;
    wherein said container body comprises:
        a first semi-shell and a second semi-shell configured to be fixed facing each other by a removable fixing system and together to define said internal compartment and said culture surface; and
        at least one outfeed opening of at least one of a transport or a culture fluid of said cells,
    wherein said first semi-shell and second semi-shell comprise respective flexible laminar sheets, at least one of which is made from a gas-permeable, waterproof and microbiologically impermeable material,
    wherein said culture surface that comprises an internal surface of at least one of said first semi-shell and second semi-shell comprises a reticular element comprising threads arranged in a warp and a weft, and
    wherein said culture surface further comprises a porous or rough three-dimensional surface of a culture element disposed in said internal compartment by adhering to at least one of said first semi-shell or second semi-shell.

2. The device according to claim 1, wherein said culture element is made from a bio-absorbable material.

3. The device according to claim 1, wherein said culture element is made from a degradable material according to pre-set degradation times.

4. The device according to claim 1, wherein said threads of said warp comprise segments of capillaries that are parallel and equal to each other, defining respective opposite homologous ends, and wherein said weft comprises at least two connection elements, each configured to connect homologous ends of said opposite homologous ends.

5. The device according to claim 4, wherein said connection elements respectively comprise an infeed and an outfeed for an auxiliary fluid arranged to flow through said segments of capillaries and through said connection elements.

6. The device according to claim 1, wherein said fixing system comprises a peelable gluing bead.

7. The device according to claim 1, wherein said fixing system comprises:
    a frame element) that delimits said internal compartment and which defines two opposite faces; and
    respective peelable gluing cords applied on each face of said opposite faces, in perimeter zones of said internal compartment, said frame element being configured to receive in removable gluing said first shell and said second shall, each one on a respective face of said opposite faces.

8. The device according to claim 1, wherein one or more of said culture surface or said culture element are configured to be directly applied to a patient.

9. The device according to claim 1, wherein said culture surface or culture element are made from materials that are degradable in a pre-set time interval.

10. The device according to claim 1, wherein said culture surface comprises a size increase system to increase a size of said culture surface.

11. The device according to claim 10, wherein said size increase system comprises a series of bends obtained in said culture surface and in relief in said internal compartment.

12. An apparatus for cell culture, comprising:
    a device for cell culture having a container body, the container body comprising,
        an internal compartment configured to contain a quantity of cells to be cultured,
        a culture surface for said cells placed in said internal compartment,
        a first semi-shell and a second semi-shell configured to be fixed facing each other by a removable fixing system and together to define said internal compartment and said culture surface,
        at least one outfeed opening of at least one of a transport or a culture fluid of said cells; and
        an introduction opening for introducing said cells to be cultured in said compartment,
    wherein said first semi-shell and second semi-shell comprise respective flexible laminar sheets, at least one of which is made from a gas-permeable, waterproof and microbiologically impermeable material,
    wherein said culture surface that comprises an internal surface of at least one of said first semi-shell and second semi-shell comprises a reticular element that includes thread arranged in a warp and a weft, and
    wherein said culture surface further comprises a porous or rough three-dimensional surface of a culture element disposed in said internal compartment by adhering to at least one of said first semi-shell or second semi-shell.

* * * * *